(12) United States Patent
Kersey et al.

(10) Patent No.: US 9,989,453 B2
(45) Date of Patent: Jun. 5, 2018

(54) TOMOGRAPHIC DETERMINATION OF SCALE BUILD-UP IN PIPES AND OTHER TANKS, CELLS, VESSELS OR CONTAINERS

(71) Applicant: CiDRA Corporate Services Inc., Wallingford, CT (US)

(72) Inventors: Alan D. Kersey, South Glastonbury, CT (US); Mark R. Fernald, Enfield, CT (US)

(73) Assignee: CiDRA CORPORATE SERVICES, INC., Wallingford, CT (US)

( * ) Notice: Subject to any disclaimer, the term of this patent is extended or adjusted under 35 U.S.C. 154(b) by 94 days.

(21) Appl. No.: 14/408,347

(22) PCT Filed: Jun. 20, 2013

(86) PCT No.: PCT/US2013/046738
§ 371 (c)(1),
(2) Date: Dec. 16, 2014

(87) PCT Pub. No.: WO2013/192387
PCT Pub. Date: Dec. 27, 2013

(65) Prior Publication Data
US 2015/0145532 A1 May 28, 2015

Related U.S. Application Data

(60) Provisional application No. 61/662,094, filed on Jun. 20, 2012.

(51) Int. Cl.
G01N 27/00 (2006.01)
G01N 17/02 (2006.01)

(52) U.S. Cl.
CPC .................... *G01N 17/02* (2013.01)

(58) Field of Classification Search
CPC .... G01N 17/02; G01N 27/221; G01N 27/226; G01N 27/22; G01N 27/223; G01N 27/2605
See application file for complete search history.

(56) References Cited

U.S. PATENT DOCUMENTS

| 4,328,707 A | 5/1982 | Clement et al. |
|---|---|---|
| 4,386,854 A | 6/1983 | Byer |
| 5,181,778 A | 1/1993 | Beller |

(Continued)

*Primary Examiner* — Jermele M Hollington
*Assistant Examiner* — Suresh K Rajaputra
(74) *Attorney, Agent, or Firm* — Ware, Fressola, Maguire & Barber LLP

(57) ABSTRACT

Apparatus is provided featuring a signal processor or processing module configured at least to: receive signaling containing information about the conductivity of a fluid contained, processed or flowing in a pipe, tank, cell or vessel having electrodes around the circumference of the pipe, tank, cell or vessel in an irregular configuration; and determine a scale build-up in the pipe, tank, cell or vessel using a tomographic processing technique, based at least partly on the signaling received. The signal processor module may be configured to provide corresponding signaling containing information about the scale build-up in the pipe, tank, cell or vessel using the tomographic processing technique, e.g., including where the corresponding signaling contains information about a chemical to be injected to control the scale build-up, including in a closed loop manner.

31 Claims, 4 Drawing Sheets

Drop in apparent conductivity with increasing scale

(56) References Cited

U.S. PATENT DOCUMENTS

| | | | |
|---|---|---|---|
| 6,078,397 A | 6/2000 | Monchalin et al. | |
| 7,466,147 B2* | 12/2008 | Stahlmann | G01N 27/226 |
| | | | 324/663 |
| 2003/0071604 A1* | 4/2003 | Lee | G01R 27/08 |
| | | | 324/72.5 |
| 2004/0130338 A1* | 7/2004 | Wang | G01N 27/20 |
| | | | 324/694 |
| 2004/0168811 A1* | 9/2004 | Shaw | E21B 37/06 |
| | | | 166/368 |
| 2008/0053204 A1 | 3/2008 | Neville et al. | |
| 2008/0163692 A1* | 7/2008 | Huang | G01F 1/663 |
| | | | 73/627 |
| 2008/0163700 A1* | 7/2008 | Huang | G01B 17/025 |
| | | | 73/861.25 |
| 2012/0098549 A1* | 4/2012 | Wang | G01N 27/026 |
| | | | 324/649 |
| 2014/0373631 A1* | 12/2014 | Davis | G01B 17/025 |
| | | | 73/627 |

* cited by examiner

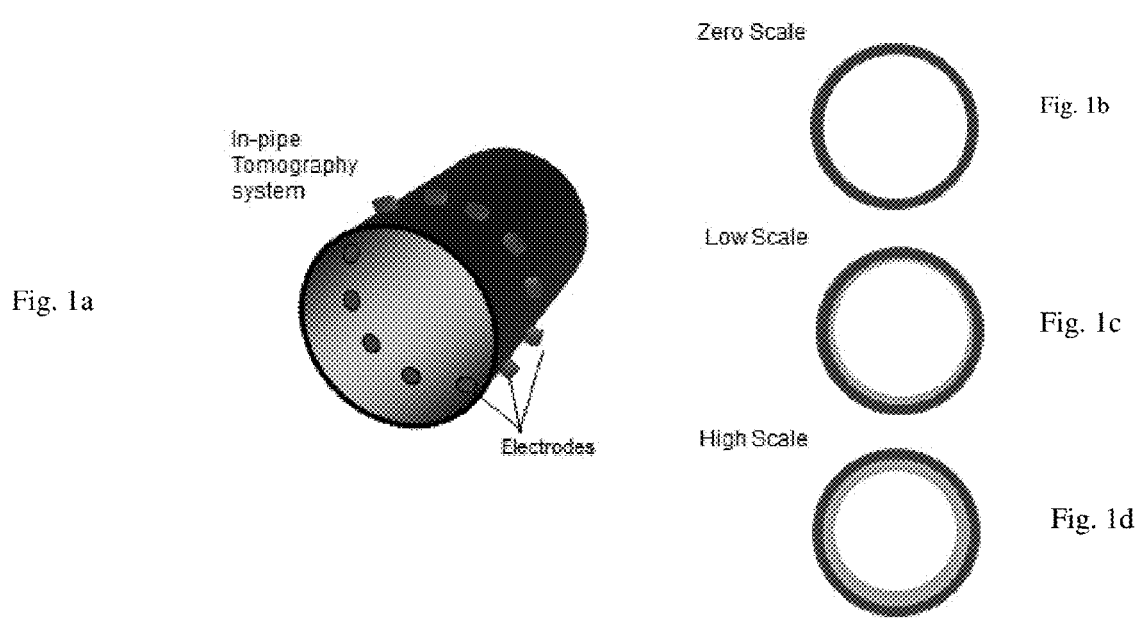
Figure 1: Concept for measuring scale (Prior art)

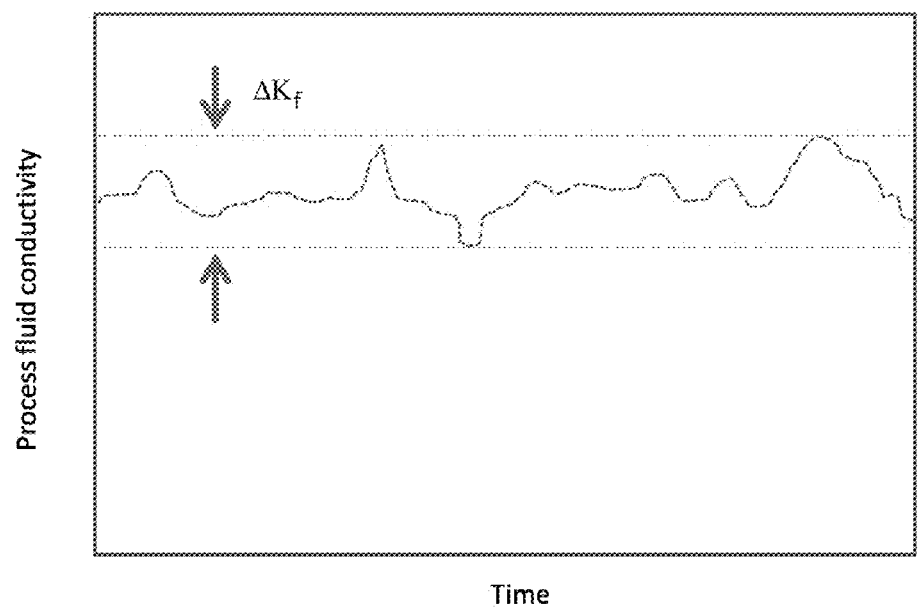
Figure 2: Variation in the conductivity of a process fluid

Figure 3: Drop in apparent conductivity with increasing scale

Apparatus 10 having a signal processor or processing module 10a configured at least to receive signaling containing information about the conductivity of a fluid contained, processed or flowing in a pipe, tank, cell or vessel having electrodes around the circumference of the pipe, tank, cell or vessel in an irregular configuration;

determine a scale build-up in the pipe, tank, cell or vessel using a tomographic processing technique, based at least partly on the signaling received; and/or provide corresponding signaling containing corresponding information about the scale build-up in the pipe, tank, cell or vessel using the tomographic processing technique, e.g., including where the corresponding signaling contains information about a chemical to be injected to control the scale build-up, including in a closed loop manner Other circuits, components or modules 10b to implement the functionality of the signal processor or processing module 10a either now known or later developed in the future, e.g., including memory modules, input/output modules, data and busing architecture and other signal processing circuits, wiring or components

Figure 6

TOMOGRAPHIC DETERMINATION OF SCALE BUILD-UP IN PIPES AND OTHER TANKS, CELLS, VESSELS OR CONTAINERS

CROSS-REFERENCE TO RELATED APPLICATIONS

This application corresponds to international patent application Ser. No. PCT/US2013/046738, filed 20 Jun. 2013, which claims benefit to provisional patent application Ser. No. 61/662,094, filed, 20 Jun. 2012 which is incorporated by reference in their entirety.

This application is related to PCT/US12/28285, filed 28 Feb. 2013, which claims benefit to provisional patent application Ser. No. 61/604,080, filed 28 Feb. 2012, which are incorporated by reference in their entirety.

This application is also related to PCT application no. PCT/US12/52074, filed 23 Aug. 2012, which claims benefit to provisional patent application Ser. No. 61/526,336, filed 23 Aug. 2011, which are incorporated by reference in their entirety.

This application is also related to PCT application no. PCT/US12/60811, filed 18 Oct. 2012, which claims benefit to provisional patent application Ser. No. 61/548,513, filed 18 Oct. 2011, which are incorporated by reference in their entirety.

BACKGROUND OF THE INVENTION

1. Field of Invention

The present invention relates to techniques for determining a scale build-up in pipes, tanks, vessels or containers; and more particular to techniques for determination of a scale build-up in pipes, tanks, vessels or containers using tomographic techniques.

2. Description of Related Art

Tomographic techniques or approaches based on the use of Electrical Resistance Tomography (ERT), Electrical Capacitance Tomography (ECT) and Electrical Impedance Tomography (EIT) are becoming widely exploited in industrial processes for the analysis of mixing in multi-phase flows, liquid interfaces and liquid-froth layers for example.

These techniques or approaches are based at least partly on the difference in conductivity or electrical (complex) permeability of materials or mediums under investigation. In such a technique, the aim is to image the cross-section of the fluid in, e.g., a pipe, to indicate:

1) The mixing of different fluidic components,
2) Air content, and/or
3) The degree/content of solids in the flow.

By way of example, the use of tomographic analysis using linear-geometry probe sensors has also been disclosed and is known in the art. In such an application, the fluid composition in the volume surrounding the probe (the measurement volume) can be visualized using tomographic processing. This type of probe has been applied to measurements taken in flotation cells, e.g., in mineral separation processes. In such an application, as with many others, scale build-up on sensor electrodes can give an erroneous tomographic image of the measurement volume.

Scale build-up on electrodes results in a layer of high resistivity material on the electrode, known as the electrode-fluid interface conductivity, as shown in FIG. 1. This layer increases in resistance (drops in conductivity) as the scale deposits build-up. By way of example, FIGS. 1b, 1c and 1d respectively show such a pipe having substantially zero scale build-up, low scale build-up, and high scale build-up.

In order to create tomographic images, it is known to use, e.g., an in-pipe tomography system as shown in FIG. 1a, and to space a set of electrodes in regular intervals around the circumference of the pipe, e.g., in a so-called regular configuration. See also that shown in FIG. 4a. The regular configuration may include, or take the form of, evenly or symmetrically spaced electrodes in regular intervals and/or electrodes having substantially the same width or length. In operation, current is sent between a pair of electrodes and the potentials generated across other pairs are monitored. When the tomographic electrode array is first deployed, the impedance between two adjacent electrodes varies with the conductivity of the fluid in the measurement volume. For a pipe-based array as shown in FIG. 1a, the conductivity of the fluid, $K_f$, fluctuates with the variability in the process fluid. In most normal or typical applications, the range in conductivity ($\Delta K_f$) of the process fluid is bounded by the constituents of fluid (in the case of mixed fluids), or the degree of dissolved or suspended particles in the flow. As an example, see the graph in FIG. 2, which shows process fluid conductivity in relation to time and the variation in the conductivity of a process fluid.

This range of variance in conductivity, $\Delta K_f$, occurs at fluid mixing/process variability time frames, typically in sub-second to minute time frames. As scale builds up on the electrodes, the electrode-fluid interface conductivity ($K_e$) drops the measured conductivity, K, of the fluid, consistent with the relationship set forth in the equation, as follows:

$$K = K_f * K_e / (K_f + K_e).$$

The measured conductivity, K, typically appears to fall over time, consistent with that set forth in the graph in FIG. 3, which shows apparent process fluid conductivity in relation to time and the drop in apparent conductivity with increasing scale, while the fluidic time-varying component remains, but is now suppressed in amplitude due to the scale build-up.

Tomographic processing algorithms are known in the art and have been developed to compensate for this scale build-up by compensating for the electrode-fluid interface conductivity, using a model that slow increments of an inputted value of the effective electrode-fluid interface conductivity $K_f$ over time to 'restore' the correct variability in the fluidic conductivity. As the scale builds up over time in an incrementing fashion, and initiates on 'clean' electrodes, some boundaries are set for electrode-fluid interface conductivity $K_e$, as follows:

e.g.: at $t=0$, $K_e=0$, and at $t_2 > t_1$, $K_e(t_2) < K_e(t_1)$.

In this way, the electrode-fluid interface conductivity $K_e$ can be inferred, and the compensation applied to a measure of the fluid conduction (and this composition).

In most industrial processes, the potential for scale build-up is known, as well as the types of deposits (e.g., calcium carbonate) that are building up.

In view of the aforementioned understanding, there is a need in the industry for a different and better way to determine the scale build-up, e.g., in a pipe, tank, cell or vessel.

SUMMARY OF THE INVENTION

According to some embodiments of the present invention, a technique is provided such that an inferred electrode-fluid interface conductivity may be taken and the scale build-up may be calculated from an a priori assessment (i.e. deduction) of the conductivity of the scale material with thickness.

According to some embodiments of the present invention, for scale build up, it has been determined that an irregular configuration of a set of electrodes around the circumference of the pipe, tank, cell or vessel may provide some important advantages. By way of example, the irregular configuration may include, or take the form of, some combination of unevenly or asymmetrically spaced electrodes in irregular intervals.

Moreover still, according to some embodiments of the present invention, the use of electrodes with differing or variable widths or lengths arranged in patterns may also be advantageous for this type of measurement, as the effective overall electrode-fluid interface conductivity will depend on the contact area of electrodes.

In operation, such techniques or approaches will allow the scale build-up in a pipe, tank, cell or vessel to be assessed, and, e.g., a chemical to be injected to control the scale build-up in a closed loop manner.

Examples of Particular Embodiments

According to some embodiments, the present invention may include, or take the form of, apparatus featuring a signal processor or processing module configured at least to:

receive signaling containing information about the conductivity of a fluid contained, processed or flowing in a pipe, tank, cell or vessel having electrodes around the circumference of the pipe, tank, cell or vessel in an irregular configuration; and determine a scale build-up in the pipe, tank, cell or vessel using a tomographic processing technique, based at least partly on the signaling received.

According to some embodiment of the present invention, the signal processor module may be configured to provide corresponding signaling containing information about the scale build-up in the pipe, tank, cell or vessel using the tomographic processing technique, e.g., including where the corresponding signaling contains information about a chemical to be injected to control the scale build-up, including in a closed loop manner.

The present invention may also include one or more of the following features:

The irregular configuration may include, or take the form of, unevenly or asymmetrically spaced electrodes in irregular intervals. By way of example, the electrodes may include a first electrode pair spaced at a first distance, and a second electrode pair spaced at a second distance that is different than the first distance.

The irregular configuration may include, or take the form of, electrodes having differing or varying widths or lengths. By way of example, the electrodes may include a first electrode pair having a first width or length, and a second electrode pair having a second width or length that is different than the first width or length.

The irregular configuration may include, or take the form of, unevenly or asymmetrically spaced electrodes in irregular intervals in combination with electrodes having differing or varying widths or lengths. By way of example, the electrodes may include a first electrode pair spaced at a first distance and having a first width or length, and a second electrode pair spaced at a second distance that is different than the first distance and having a second width or length that is different than the first width or length. Alternatively, and by way of further example, the electrodes may include a first electrode pair spaced at a first distance, and a second electrode pair spaced at a second distance that is different than the first distance; and also include a third electrode pair having a first width or length, and a fourth electrode pair having a second width or length that is different than the first width or length. Embodiments are envisioned, and the scope of the invention is intended to include, using other types or kinds of irregular configurations within the spirit of the underlying invention.

The signal processor module may be configured to determine the scale build-up in the pipe, tank, cell or vessel using the tomographic processing technique, based at least partly on determining the conductivity of the fluid between the electrodes, which depends on the conductivity of the fluid through a path between the electrodes and twice an electrode-fluid interface conductivity or scale layer.

The signal processor module may be configured to determine the scale build-up in the pipe, tank, cell or vessel using the tomographic processing technique, based at least partly on assessing an average fluid conductivity in order to yield a series of equations that can be solved for determining an electrode-fluid interface conductivity or scale layer.

The signal processor module may be configured to determine the electrode-fluid interface conductivity or scale layer based at least partly on the contact area of electrodes.

The apparatus may include or comprise the irregular configuration having electrodes with unevenly or asymmetrically spaced electrodes in irregular intervals.

The apparatus may include or comprise the irregular configuration having electrodes with differing or varying widths or lengths.

The apparatus may include or comprise the irregular configuration having electrodes with unevenly or asymmetrically spaced electrodes in irregular intervals in combination with electrodes with differing or varying widths or lengths.

The signal processor or processing module may be configured with at least one processor and at least one memory including computer program code, the at least one memory and computer program code configured, with the at least one processor, to cause the apparatus at least to receive the signaling and determine the scale build-up in the pipe, tank, cell or vessel using the tomographic processing technique, based at least partly on the signaling received.

The tomographic processing technique may include electrical resistance tomography (ERT), electrical capacitance tomography (ECT), or electrical impedance tomography (EIT).

The Method

According to some embodiments, the present invention may include, or take the form of, a method or process that includes steps for receiving with a signal processor or processing module signaling containing information about the conductivity of a fluid contained, processed or flowing in a pipe, tank, cell or vessel having electrodes around the circumference of the pipe, tank, cell or vessel in an irregular configuration; and determining a scale build-up in the pipe, tank, cell or vessel using a tomographic processing technique, based at least partly on the signaling received.

The method may also include one or more of the features set forth herein, according to some embodiments of the present invention.

BRIEF DESCRIPTION OF THE DRAWING

The drawing includes FIGS. 1-6, which are not necessarily drawn to scale, as follows:

FIG. 1 shows an in-pipe tomography system having electrodes evenly spaced about the circumference of a pipe for measuring scale build-up in the pipe that is known in the art.

FIG. 2 shows a graph of process fluid conductivity in relation to time and the variation in the conductivity of a process fluid, consistent with that known in the art.

FIG. 3 shows a graph of apparent process fluid conductivity in relation to time and the drop in the conductivity with increasing scale build-up, consistent with that known in the art.

FIG. 6 is a block diagram of apparatus having a signal processor or processing module configured to implement some embodiments of the present invention.

DETAILED DESCRIPTION OF BEST MODE OF THE INVENTION

FIG. 5

Figure 4:
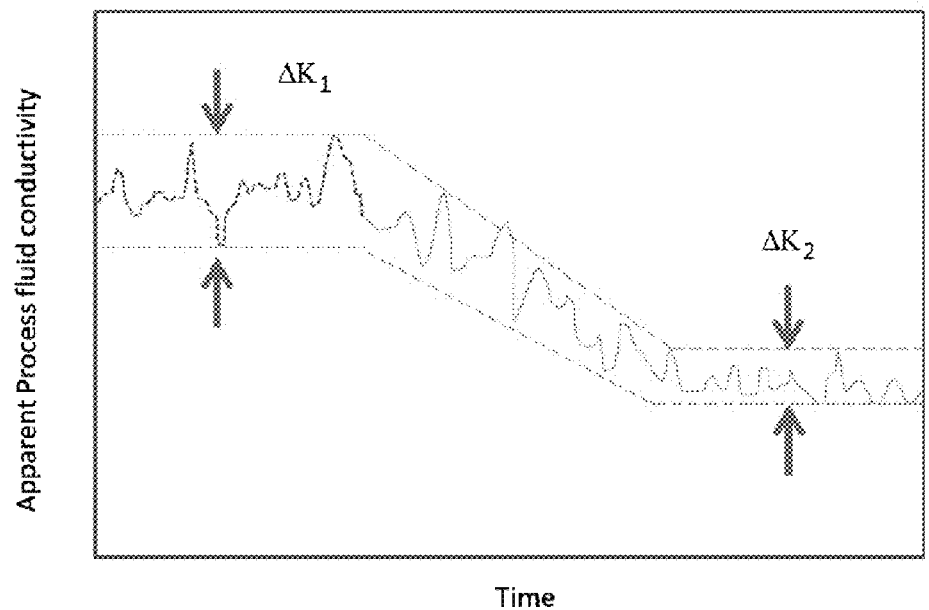
FIG. 4 is a diagram of a pipe having electrodes evenly spaced about the circumference of a pipe, consistent with that known in the art.
Figure 5:
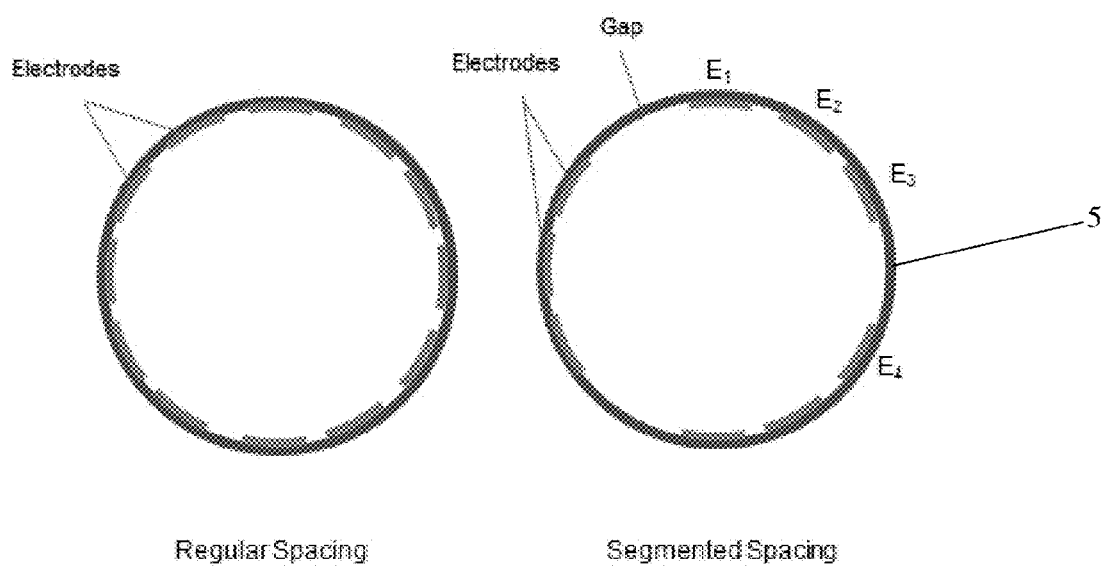
FIG. 5 is a diagram of a pipe having electrodes using segmented spacing, or generally irregularly spaced electrodes, and/or electrodes of differing widths or lengths about the circumference of a pipe for measuring scale build-up, according to some embodiments of the present invention.

FIG. 5 shows an example of electrodes, some of which are labeled E1, E2, E3, E4, having segmented spacing in an irregular configuration, according to some embodiments of the present invention. The electrodes E1, E2, E3, E4 are shown in the irregular configuration on the inside wall of a pipe 5. Electrodes pairs are separated by a respective gap, where the gap between some electrodes pairs like E1 and E2 are different than the gap between other electrode pairs like electrodes E3 and E4, so as to form the segmented spacing. It is understood that the circumference of the inside wall of the pipe 5 is known, and the associate gaps between electrodes pairs like E1 and E2 and the other electrode pairs like electrodes E3 and E4 are also known. As shown, the distance between the electrodes pair E1 and E2 may be defined by a path P, and the distance between the electrodes pair E3 and E4 may be defined by a path 2P, e.g., which is about twice in distance or length than path P.

In FIG. 5, the conductivity measured between two closely-spaced electrodes, like E1 and E2, may be determined by the conductivity of the fluid through the path P, and twice the electrode-fluid interface conductivity (scale layer). In comparison, the conductivity between two less closely-spaced electrodes, like E3 and E4 (which are farther apart from one another), may be determined by the conductivity of the fluid through the path approximately 2P in length, and twice the electrode-fluid interface conductivity (scale layer). As a person skilled in the art would appreciate, if the average fluid conductivity is assessed using tomographic processing, this can be used to yield a series of equations that can be solved for determining the electrode-fluid interface conductivity, consistent and in accordance with some embodiments of the present invention.

FIG. 6: The Basic Apparatus 10

FIG. 6 shows apparatus 10 having a signal processor or processing module 10a for implementing the basic signal processing functionality according to some embodiments of the present invention. The signal processor or processing module 10a may be configured at least to receive signaling containing information about the conductivity of a fluid contained, processed or flowing in a pipe, tank, cell or vessel having electrodes around the circumference of the pipe, tank, cell or vessel in an irregular configuration; and determine a scale build-up in the pipe, tank, cell or vessel using a tomographic processing technique, based at least partly on the signaling received.

By way of example, the signaling may be received from the irregular configuration, or from some other signal processing device that receives the signaling, processes the same, and provides some further processed signaling containing information about the conductivity of the fluid contained, processed or flowing in the pipe, tank, cell or vessel having the electrodes around the circumference of the pipe, tank, cell or vessel in the irregular configuration. By way of example, the further processed signaling may include amplifying, filtering, smoothing or some other processing of the signaling received from the irregular configuration.

The signal processor or processing module 10a may also be configured to provide corresponding signaling containing corresponding information about the scale build-up in the pipe, tank, cell or vessel using the tomographic processing technique, e.g., including where the corresponding signaling contains information about a chemical to be injected to control the scale build-up, including in a closed loop manner. The scope of the invention is not intended to be limited to the type or kind of use of the corresponding signaling containing information about the scale build-up in the pipe, tank, cell or vessel, including for further processing, printing or displaying, as well as for other types or kinds of uses either now known or later developed in the future.

Further, the scope of the invention is not intended to be limited to the type or kind of fluid contained, processed or flowing in the pipe, tank, cell or vessel. For example, the scope of the invention is intended to include processing fluids that are either now known or later developed in the future. Moreover, the scope of the invention is intended to include sensing and determining the scale build-up in pipes, tanks, cells, vessels, etc., that are either now known or later developed in the future. Moreover still, the scope of the invention is not intended to be limited to the type or kind of industrial process of which the fluid is being processed, including a process or processes that is or are either now known or later developed in the future.

The apparatus 10 may also include other circuits, components or modules 10b to implement the functionality of the signal processor or processing module 10a either now known or later developed in the future, e.g., including memory modules, input/output modules, data and busing architecture and other signal processing circuits, wiring or components, consistent with that known by a person skilled in the art, and/or consistent with that set forth herein.

Signal Processor or Signal Processing Module 10a

By way of example, and consistent with that described herein, the functionality of the signal processor or processing module 10a may be implemented to receive the signaling, process the signaling, and/or provide the corresponding signaling, using hardware, software, firmware, or a combination thereof, although the scope of the invention is not intended to be limited to any particular embodiment thereof. In a typical software implementation, the signal processor or processing module 10a may include, or take the form of, one or more microprocessor-based architectures having a microprocessor, a random access memory (RAM), a read only memory (ROM), input/output devices and control, data and address busing architecture connecting the same. A person skilled in the art would be able to program such a microprocessor-based implementation to perform the functionality set forth herein, as well as other functionality described herein without undue experimentation. The scope of the invention is not intended to be limited to any particular implementation using technology either now known or later developed in the future. Moreover, the scope of the invention is intended to include a signal processor, device or module 10a as either part of the aforementioned apparatus, as a stand alone module, or in the combination with other circuitry for implementing another module.

Techniques for receiving signaling in such a signal processor or processing module 10a are known in the art, and the scope of the invention is not intended to be limited to any particular type or kind thereof either now known or later developed in the future. Based on this understanding, a person skilled in the art would appreciate, understand and be able to implement and/or adapt the signal processor or processing module 10a without undue experimentation so as to receive signaling containing information about the conductivity of a fluid flowing in a pipe, tank, cell or vessel having electrodes around the circumference of the pipe, tank, cell or vessel in an irregular configuration, consistent with that set forth herein.

Techniques, including techniques based on tomography or tomographic processing techniques, for determining information based on analyzing or processing signaling received in such a signal processor or processing module 10a are also known in the art, and the scope of the invention is not intended to be limited to any particular type or kind thereof either now known or later developed in the future. Based on this understanding, a person skilled in the art would appreciate, understand and be able to implement and/or adapt the signal processor or processing module 10a without undue experimentation so as to determine a scale build-up in the pipe, tank, cell or vessel using a tomographic processing technique, based at least partly on the signaling received, consistent with that set forth herein.

It is also understood that the apparatus 10 may include one or more other modules, components, processing circuits, or circuitry 10b for implementing other functionality associated with the underlying apparatus that does not form part of the underlying invention, and thus is not described in detail herein. By way of example, the one or more other modules, components, processing circuits, or circuitry may include random access memory, read only memory, input/output circuitry and data and address buses for use in relation to implementing the signal processing functionality of the signal processor, or devices or components, etc.

Tomography or Tomographic Processing Techniques

Tomography or tomographic processing techniques are known in the art, and generally understood to refer to imaging by sections or sectioning, through the use of any kind of penetrating wave. A device used in tomography is called a tomograph, while the image produced is a tomogram. Such methods or techniques may be used, e.g., in radiology, archeology, biology, geophysics, oceanography, materials science, astrophysics, quantum information and other sciences. In most cases, such methods or techniques may be based on the mathematical procedure called tomographic reconstruction. Tomographic reconstruction algorithms are known in the art for determining the imaging by sections or sectioning, through the use of any kind of penetrating wave. By way of example, the reader is referred to U.S. Pat. Nos. 6,078,397; 5,181,778; 4,386,854; and 4,328,707, which all relate to tomographic techniques and are all incorporated by reference in their entirety. The scope of the invention is not intended to be limited to the type or kind of tomographic reconstruction algorithms, including those based at least partly on using ultrasonic waves, either now known or later developed in the future.

See also the aforementioned PCT application no. PCT/US12/52074, filed 23 Aug. 2012, as well as PCT application no. PCT/US12/60811, filed 18 Oct. 2012, which disclose applications based at least partly on using a tomography or tomographic processing technique, which was developed and is owned by the assignee of the instant patent application, and which is hereby incorporated by reference in its entirety.

Moreover, embodiments are envisioned, and the scope of the invention is intended to include, using other types or kinds of tomography or tomographic processing technique either now known or later developed in the future. Finally, the scope of the invention is not intended to be limited to any particular type or kind of tomography or tomographic processing technique either now known or later developed in the future.

A person skilled in the art without undue experimentation would be able to adapt one or more of the aforementioned tomography or tomographic processing technique in order to implement the present invention, including to configure a signal processing module at least to receive signaling containing information about the conductivity of a fluid contained, processed or flowing in a pipe, tank, cell or vessel having electrodes around the circumference of the pipe, tank, cell or vessel in an irregular configuration; and determine a scale build-up in the pipe, tank, cell or vessel using a tomographic processing technique, based at least partly on the signaling received.

Applications

By way of example, the present invention may be used in, or form part of, or used in conjunction with, industrial processes like a mineral extraction processing system for extracting or separating minerals in a fluidic medium that are either now known or later developed in the future, including any mineral process, such as those related to processing substances or compounds that result from inorganic processes of nature and/or that are mined from the ground, as well as including either other extraction processing systems or other industrial processes, where the extraction, or separating, or sorting, or classification, of product by size, or density, or some electrical characteristic, is critical to overall industrial process performance.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. Apparatus for providing a determination of scale build-up on an inside wall of a pipe, tank, cell, vessel or container, comprising:
   a signal processor module configured to:
   receive signaling containing information about the conductivity of a fluid contained, processed or flowing in a pipe, tank, cell, vessel or container having electrodes around the circumference of the pipe, tank, cell, vessel or container in an irregular configuration; and
   determine corresponding signaling containing information about a scale build-up on an inside wall of the pipe, tank, cell, vessel or container using a tomographic processing technique, based at least partly on the signaling received.

2. Apparatus according to claim 1, wherein the irregular configuration comprises, or take the form of, unevenly or asymmetrically spaced electrodes in irregular intervals on the inside wall of the pipe, tank, cell, vessel or container, including a first electrode pair spaced at a first distance, and a second electrode pair spaced at a second distance that is different than the first distance.

3. Apparatus according to claim 1, wherein the irregular configuration comprises, or take the form of, electrodes having differing or varying widths or lengths, including a first electrode pair having a first width or length, and a second electrode pair having a second width or length that is different than the first width or length.

4. Apparatus according to claim 1, wherein the irregular configuration comprises, or takes the form of, unevenly or asymmetrically spaced electrodes in irregular intervals in combination with electrodes having differing or varying widths or lengths, including
   either a first electrode pair spaced at a first distance and having a first width or length, and a second electrode pair spaced at a second distance that is different than the first distance and having a second width or length that is different than the first width or length; or
   a first electrode pair spaced at a first distance, a second electrode pair spaced at a second distance that is different than the first distance, a third electrode pair having a first width or length, and a fourth electrode pair having a second width or length that is different than the first width or length.

5. Apparatus according to claim 1, wherein the signal processor module is configured to determine the scale build-up in the pipe, tank, cell or vessel using the tomographic processing technique, based at least partly on determining the conductivity of the fluid between the electrodes, which depends on the conductivity of the fluid through a path between the electrodes and twice an electrode-fluid interface conductivity or scale layer.

6. Apparatus according to claim 5, wherein the signal processor module is configured to determine the scale build-up in the pipe, tank, cell or vessel using the tomographic processing technique, based at least partly on assessing an average fluid conductivity in order to yield a series of equations that can be solved for determining an electrode-fluid interface conductivity or scale layer.

7. Apparatus according to claim 5, wherein the signal processor module is configured to determine the electrode-fluid interface conductivity or scale layer based at least partly on the contact area of electrodes.

8. Apparatus according to claim 1, wherein the apparatus further comprises the irregular configuration having unevenly or asymmetrically spaced electrodes in irregular intervals.

9. Apparatus according to claim 1, wherein the apparatus further comprises the irregular configuration having electrodes with differing or varying widths or lengths.

10. Apparatus according to claim 1, wherein the apparatus further comprises the irregular configuration having unevenly or asymmetrically spaced electrodes in irregular intervals in combination with electrodes having differing or varying widths or lengths.

11. Apparatus according to claim 1, wherein the signal processor module is configured to provide the corresponding signaling containing information about the scale build-up in the pipe, tank, cell or vessel using the tomographic processing technique.

12. Apparatus according to claim 11, wherein the corresponding signaling contains information about a chemical to be injected to control the scale build-up, including in a closed loop manner.

13. Apparatus according to claim 1, wherein the signal processor module is configured with at least one processor and at least one memory including computer program code, the at least one memory and computer program code configured, with the at least one processor, to cause the apparatus at least to receive the signaling and determine the scale build-up in the pipe, tank, cell or vessel using the tomographic processing technique, based at least partly on the signaling received.

14. A method for providing a determination of scale build-up on an inside wall of a pipe, tank, cell, vessel or container, comprising:
   receiving with a signal processor module signaling containing information about the conductivity of a fluid contained, processed or flowing in a pipe, tank, cell, vessel or container having electrodes around the circumference of the pipe, tank, cell or vessel in an irregular configuration; and
   determining with the signal processor module corresponding signaling containing information about a scale build-up on an inside wall of the pipe, tank, cell, vessel or container using a tomographic processing technique, based at least partly on the signaling received.

15. A method according to claim 14, wherein the method comprises configuring the irregular configuration with unevenly or asymmetrically spaced electrodes in irregular intervals on the inside wall of the pipe, tank, cell, vessel or container.

16. A method according to claim 14, wherein the method comprises configuring the irregular configuration with electrodes having differing or varying widths or lengths.

17. A method according to claim 14, wherein the method comprises configuring the irregular configuration with unevenly or asymmetrically spaced electrodes in irregular intervals in combination with electrodes having differing or varying widths or lengths.

18. A method according to claim 14, wherein the method comprises configuring the signal processor module to determine the scale build-up in the pipe, tank, cell or vessel using the tomographic processing technique, based at least partly on determining the conductivity of the fluid between the electrodes, which depends on the conductivity of the fluid through a path between the electrodes and twice an electrode-fluid interface conductivity or scale layer.

19. A method according to claim 18, wherein the method comprises configuring the signal processor module to determine the scale build-up in the pipe, tank, cell or vessel using the tomographic processing technique, based at least partly on assessing an average fluid conductivity in order to yield a series of equations that can be solved for determining an electrode-fluid interface conductivity or scale layer.

20. A method according to claim 18, wherein the method comprises configuring the signal processor module to determine the electrode-fluid interface conductivity or scale layer based at least partly on the contact area of electrodes.

21. A method according to claim 15, wherein the method comprises configuring the unevenly or asymmetrically spaced electrodes at least in the form of a first electrode pair spaced at a first distance, and a second electrode pair spaced at a second distance that is different than the first distance.

22. A method according to claim 16, wherein the method comprises configuring the electrodes having differing or varying widths or lengths at least in the form of a first electrode pair having a first width or length, and a second electrode pair having a second width that is different than the first width or length.

23. A method according to claim 17, wherein the method comprises configuring the unevenly or asymmetrically spaced electrodes and the electrodes having differing or varying widths or lengths at least in the form of
 either a first electrode pair spaced at a first distance and having a first width or length, and a second electrode pair spaced at a second distance that is different than the first distance and having a second width or length that is different than the first width or length, or
 a first electrode pair spaced at a first distance, and a second electrode pair spaced at a second distance that is different than the first distance; and a third electrode pair having a first width or length, and a fourth electrode pair having a second width or length that is different than the first width or length.

24. A method according to claim 14, wherein the method comprises configuring the signal processor module to provide the corresponding signaling containing information about the scale build-up in the pipe, tank, cell or vessel using the tomographic processing technique.

25. A method according to claim 24, wherein the corresponding signaling contains information about a chemical to be injected to control the scale build-up, including in a closed loop manner.

26. A method according to claim 14, wherein the method comprises configuring the signal processor module with at least one processor and at least one memory including computer program code, the at least one memory and computer program code configured, with the at least one processor, to cause the signal processor module at least to receive the signaling and determine the scale build-up in the pipe, tank, cell or vessel using the tomographic processing technique, based at least partly on the signaling received.

27. Apparatus for providing a determination of scale build-up on an inside wall of pipes, tanks, cells, vessels or containers, comprising:
 means for receiving with a signal processor module signaling containing information about the conductivity of a fluid contained, processed or flowing in a pipe, tank, cell, vessel or container having electrodes around the circumference of the pipe, tank, cell or vessel in an irregular configuration; and
 means for determining with the signal processor module corresponding signaling containing information about a scale build-up on an inside wall of the pipe, tank, cell, vessel or container using a tomographic processing technique, based at least partly on the signaling received.

28. Apparatus according to claim 27, wherein the irregular configuration comprises some combination of unevenly or asymmetrically spaced electrodes in irregular intervals on the inside wall of the pipe, tank, cell, vessel or container, and/or electrodes having differing or varying widths or lengths on the inside wall of the pipe, tank, cell, vessel or container.

29. Apparatus according to claim 27, wherein the apparatus comprises means for providing the corresponding signaling containing information about the scale build-up in the pipe, tank, cell or vessel using the tomographic processing technique, including where the corresponding signaling contains information about a chemical to be injected to control the scale build-up, including in a closed loop manner.

30. Apparatus according to claim 1, wherein the tomographic processing technique is based at least partly on one or more of the following techniques: electrical resistance tomography (ERT), electrical capacitance tomography (ECT), or electrical impedance tomography (EIT).

31. A method according to claim 14, wherein the tomographic processing technique is based at least partly on one or more of the following techniques: electrical resistance tomography (ERT), electrical capacitance tomography (ECT), or electrical impedance tomography (EIT).

* * * * *